(12) United States Patent
Humbert et al.

(10) Patent No.: US 9,523,651 B2
(45) Date of Patent: Dec. 20, 2016

(54) INTEGRATED CIRCUIT COMPRISING A GAS SENSOR

(71) Applicant: ams International AG, Rapperswil-Jona (CH)

(72) Inventors: Aurelie Humbert, Brussels (BE); Roel Daamen, Herkenbosch (NL)

(73) Assignee: AMS INTERNATIONAL AG, Rapperswil-Jona (CH)

( * ) Notice: Subject to any disclaimer, the term of this patent is extended or adjusted under 35 U.S.C. 154(b) by 51 days.

(21) Appl. No.: 14/023,332

(22) Filed: Sep. 10, 2013

(65) Prior Publication Data
US 2014/0070825 A1    Mar. 13, 2014

(51) Int. Cl.
| G01R 27/08 | (2006.01) |
| --- | --- |
| G01N 27/04 | (2006.01) |
| G01N 27/02 | (2006.01) |
| G01N 27/12 | (2006.01) |

(52) U.S. Cl.
CPC .............. *G01N 27/04* (2013.01); *G01N 27/02* (2013.01); *G01N 27/125* (2013.01)

(58) Field of Classification Search
CPC ...... G01N 27/04; G01N 27/02; G01N 27/223; G01N 27/125
USPC ........................................ 324/693, 694, 663
See application file for complete search history.

(56) References Cited

U.S. PATENT DOCUMENTS

| 4,429,343 | A | 1/1984 | Freud |
| --- | --- | --- | --- |
| 6,222,376 | B1 | 4/2001 | Tenney, III |
| 6,690,569 | B1 | 2/2004 | Mayer et al. |
| 7,222,531 | B2 | 5/2007 | Isogai et al. |
| 8,357,958 | B2 * | 1/2013 | Cummins ............ G01N 27/223 257/253 |
| 8,786,441 | B2 * | 7/2014 | Yang et al. ................. 340/572.1 |

FOREIGN PATENT DOCUMENTS

| DE | 101 33 997 A1 | 2/2003 |
| --- | --- | --- |
| EP | 2420826 A1 * | 2/2012 |
| GB | 2 365 217 A | 2/2002 |
| WO | 2007/057794 A1 | 5/2007 |

OTHER PUBLICATIONS

Eranna, G., et al; "Oxide Materials for Development of Integrated Gas Sensors—A Comprehensive Review"; Critical Reviews in Solid State and Materials Sciences, 29:3; pp. 111-188; downloaded Jan. 27, 2009 (Jul. 1, 2004).
Bai, Hua, et al; "Gas Sensors Based on Conducting Polymers"; Sensors 2007, No. 7; pp. 267-307.
Extended European Search Report for Application No. 12184015.1 (Feb. 11, 2013).

\* cited by examiner

*Primary Examiner* — Amy He
(74) *Attorney, Agent, or Firm* — McDermott Will & Emery LLP

(57) ABSTRACT

An integrated circuit and a method of making the same. The integrated circuit includes a semiconductor substrate. The integrated circuit also includes an electrical impedance based gas sensor located on the substrate. The sensor includes first and second electrically conductive sensor electrodes. Each sensor electrode is enclosed in an electrically conductive corrosion protection material. The sensor also includes a gas sensitive material located between the sensor electrodes. The impedance of the gas sensitive material is sensitive to a gas to be sensed.

14 Claims, 4 Drawing Sheets

INTEGRATED CIRCUIT COMPRISING A GAS SENSOR

CROSS-REFERENCE TO RELATED APPLICATIONS

This application claims the priority under 35 U.S.C. §119 of European patent application no. 12184015.1, filed on Sep. 12, 2012, the contents of which are incorporated by reference herein.

BACKGROUND OF THE INVENTION

This invention relates to an integrated circuit comprising a gas sensor.

Nowadays, integrated circuits may comprise a plethora of different sensors, such as ambient light (AL) sensors, temperature (T) sensors, gas sensors, relative humidity (RH) sensors, specific analyte detection sensors, and so on.

Integrated circuits of this kind have a wide range of applications. For example, they can be used in the field of supply chain management to track and monitor the freshness of food and beverages. They can also be used as environmental sensors, for example as part of a heating, ventilation and air conditioning (HVAC) system in an automobile or in a building (e.g. a Smart Building). Additional applications include those in agricultural (e.g. the sensing of environmental conditions in greenhouses) or in medical fields. Their provision in mobile communications devices such as mobile telephones, tablets or laptops can also enable a wide range of further applications that require measurements of local environmental factors.

The provision of sensors in integrated circuits of this kind allows devices to be produced that have a small form factor. For example, due to their small form factor, integrated circuits incorporating one or more sensors can be included in Radio Frequency Identification (RFID) tags, allowing for easy programming and readout.

Moreover, it allows large numbers of sensors to be manufactured cheaply, using established semiconductor processing techniques.

FIG. 1 illustrates an example of an integrated circuit comprising a gas sensor. The integrated circuit includes a semiconductor substrate 2. The substrate typically comprises various components and circuitry, including, for example CMOS transistors and/or other devices. These components can be formed in the substrate 2 using standard front end of line (FEOL) processes.

The integrated circuit also includes a metallization stack 4. Metallization stacks, which are well known in the art of semiconductor device manufacturing, typically include a plurality of dielectric layers containing patterned metal features. These metal features form interconnections for connecting together the various components of the integrated circuit formed in the substrate.

The integrated circuit further includes a passivation stack 6. The passivation stack 6 can include one or more layers forming a protective covering for the metallization stack 4 against, for example, oxidation of the metal features therein.

In the example shown in FIG. 1, the gas sensor includes a pair of capacitor electrodes 10. The electrodes 10, shown in cross section in FIG. 1, are arranged as a set of interdigitated fingers. For further examples of sensors using such an electrode configuration see U.S. Pat. No. 7,222,531, U.S. Pat. No. 6,690,569, U.S. Pat. No. 4,429,343 and U.S. Pat. No. 6,222,376). The electrodes are electrically conductive, and can comprise a metal such as aluminium (Al) or tungsten (W). The electrodes 10 are formed directly on the passivation stack 6 using the same kind of back end of line (BEOL) processes (deposition, lithography, etching) that are used to form the metal features in the metallization stack 4.

The gas sensor also includes a gas sensitive layer 12. The gas sensitive layer 12 has a dielectric constant that is sensitive to a gas to be sensed. The type of gas sensitive material that is used can thus be chosen in accordance with the target gas. In operation, the dielectric constant of the gas sensitive layer 12 varies in accordance with the levels of the target gas that are present in the vicinity of the sensor. These variations in dielectric constant can be detected as changes in the capacitance of the capacitor electrodes 12. Hence, the target gas can be detected.

Since the capacitor electrodes 10 are provided outside the passivation stack 6, they may be susceptible to corrosion. Because of this, the gas sensor further includes a protective layer 8, which acts to prevent corrosion of the electrodes 10. The protective layer 10 comprises an oxide such as $TaO_5$, which is electrically insulating.

SUMMARY OF THE INVENTION

Aspects of the invention are set out in the accompanying independent and dependent claims. Combinations of features from the dependent claims may be combined with features of the independent claims as appropriate and not merely as explicitly set out in the claims.

According to an aspect of the invention, there is provided an integrated circuit. The integrated circuit includes a semiconductor substrate. The integrated circuit also includes an electrical impedance based gas sensor located on the substrate. The sensor includes first and second electrically conductive sensor electrodes. Each sensor electrode is enclosed in an electrically conductive corrosion protection material. The sensor also includes a gas sensitive material located between the sensor electrodes. The impedance of the gas sensitive material is sensitive to a gas to be sensed.

According to another aspect of the invention, there is provided a method of making an integrated circuit. The method includes providing a semiconductor substrate. The method also includes forming an electrical impedance based gas sensor on the substrate. The sensor includes first and second electrically conductive sensor electrodes. Each sensor electrode is enclosed in an electrically conductive corrosion protection material. The method further includes depositing a gas sensitive material located between the sensor electrodes. The impedance of the gas sensitive material is sensitive to a gas to be sensed.

Embodiments of this invention can allow the provision of an integrated circuit including a gas sensor that is impedance based. By using impedance based measurements (capacitance and resistance) across the sensor electrodes, the performance (e.g. accuracy) of the sensor can be improved compared to sensors that rely only on measurements of capacitance. Additionally, an alternative range of gas sensitive materials (namely those materials for which the appropriate transducing principle involved is impedance based) is made available.

The sensor electrodes are each enclosed in an electrically conductive corrosion protection material. Accordingly, the sensor electrodes are protected in a manner that allows resistance measurements to be made between the sensor electrodes.

Various alternative configurations are envisaged for the sensor electrodes enclosed in the electrically conductive corrosion protection material. It is noted that in contrast to the protective layer 8 described in relation to FIG. 1, the electrically conductive corrosion protection material enclosing the sensor first electrode cannot be integrally formed with the electrically conductive corrosion protection material enclosing the second sensor electrode, since otherwise this would short circuit the gas sensitive material, preventing operation of the sensor.

In one example, each sensor electrode enclosed in an electrically conductive corrosion protection material can include a stack of layers. In this way, at least part of the corrosion protection material can conveniently be formed by the deposition of one or more layers, which can then be patterned to form the stack. The stack can include a first layer of the electrically conductive corrosion protection material. This layer can, in some examples, be provided directly onto a passivation stack on a metallization stack on the substrate. An electrically conductive electrode layer can be provided on the first layer of the electrically conductive corrosion protection material. In some examples, the stack can include a second layer of the electrically conductive corrosion protection material on the electrically conductive electrode layer. This second layer can provide corrosion protection for the upper surface of the sensor electrode.

The sidewalls of the stack can be covered by sidewall spacers comprising the electrically conductive corrosion protection material. The sidewall spacers can be formed in a manner that is similar to that used to provide the spacers of a MOS transistor gate electrode.

The stack, either with or without the second layer of the electrically conductive corrosion protection material on the electrically conductive electrode layer, can be coated with a further layer of the electrically conductive corrosion protection material. This further layer can cover the sidewalls of the stack. Sections of the further layer of the electrically conductive corrosion protection material located between the first and second sensor electrodes can be etched away to prevent short circuiting of the gas sensitive material.

The sensor electrodes can be arranged as a plurality of interdigitated fingers. This allows the electrodes to be placed in close proximity to each other while also ensuring that they have a large surface area. Both of the factors can increase the sensitivity of the sensor.

The sensor electrodes can comprise a metal. In some examples, the sensor electrodes can comprise Al or an AlCu alloy, or W. These materials ease the manufacture of the integrated circuit because Al and Cu are commonly used in back end of line (BEOL) processing. The manufacture of the sensor can therefore conveniently be integrated into BEOL metallization processes that were established by the industry primarily for the purpose of forming interconnects in metallization stacks, and not components such a gas sensors.

Suitable materials for the corrosion protection material 14 include, for example, TiN. Other examples for the corrosion protection material 14 include TaN, TiWN and also selectively deposited materials like e-less ternary materials such as CoWP, CoWB, NiMoP, NiMoB or multilayers of those ternary alloys.

According to a further aspect of the invention, there can be provided a Radio Frequency Identification (RFID) Tag including an integrated circuit of the kind described above.

According to a further aspect of the invention, there can be provided a mobile communications device including an integrated circuit of the kind described above.

According to another aspect of the invention, there can be provided a heating, ventilation and air conditioning (HVAC) system including one or more integrated circuits of the kind described above.

BRIEF DESCRIPTION OF THE DRAWINGS

Embodiments of the present invention will be described hereinafter, by way of example only, with reference to the accompanying drawings in which like reference signs relate to like elements and in which.

DETAILED DESCRIPTION

Embodiments of the present invention are described in the following with reference to the accompanying drawings.

Embodiments of this invention allow the provision of an integrated circuit that includes an electrical impedance based gas sensor located on a semiconductor substrate. In order to prevent corrosion of the sensor electrodes of such a gas sensor, the sensor electrodes are enclosed in an electrically conductive corrosion protection material. Because the corrosion protection material is electrically conductive, impedance based measurements (in particular, resistance measurements) used in the sensor are not inhibited by electrical isolation of the sensor electrodes in a corrosion protection material comprising an electrically resistive substance such as an oxide or other dielectric.

The provision of an electrically conductive corrosion protection material in the described sensor involves a number of challenges. One of these challenges is to enclose the sensor electrodes in a manner that does not lead to short-circuiting of the gas sensitive material of the sensor during resistance measurements between the sensor electrodes. Another challenge is to provide the material in a manner that does not overly impact on the manufacturing process for the integrated circuit as a whole (for example, the manufacturing process should not involve an undue number of additional processing steps in, for example, the back end of line).

Figure 2:
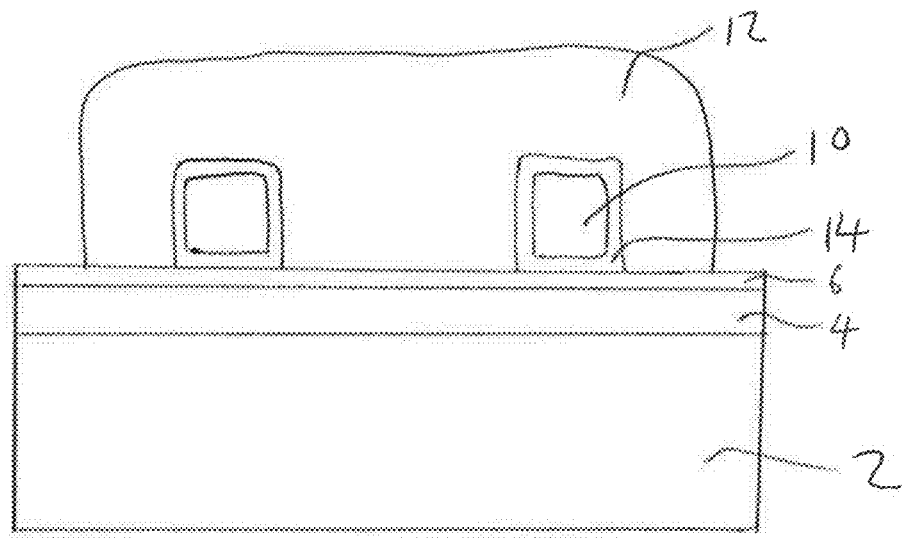
FIG. 2 shows an example of an integrated circuit including an environmental sensor according to an embodiment of the invention.

A first example of an integrated circuit in accordance with an embodiment of this invention is schematically illustrated in FIG. 2. The integrated circuit includes a substrate 2. The substrate 2 can, for example, comprise silicon. In some examples, the substrate 2 can include various components and circuitry, such as CMOS transistors and/or other devices. These components can be formed in the substrate 2 using standard front end of line (FEOL) processing steps.

In some examples, the above mentioned components can form features such as control circuitry for operating the gas sensor, memory for storing readings taken by the gas sensor and/or an analogue to digital converter (ADC) for converting readings taken by the gas sensor into the digital domain. For the purposes of clarity, these further components are not illustrated in the example of FIG. 2.

As shown in FIG. 2, the integrated circuit is provided with a metallization stack 4. The metallization stack 4 includes a plurality of layers including dielectric layers containing patterned metal features. These metal features can provide interconnects for the various components of the integrated circuit, such as those provided in the substrate 2 and, indeed the gas sensor itself. The metallization stack 4 is provided with a passivation stack 6. The passivation stack serves to protect the underlying layers from damage caused by, for example, oxidation of the metal features thereof. The passivation stack 6 can include, for example, one or more oxide layers (e.g., high density plasma oxide (HDP)) and a capping layer comprising a material such as $Si_3N_4$.

In the present example and in the subsequent examples described below, the features of the gas sensor are provided outside the passivation layer 6. However, it will be appreciated that this configuration is not essential to the present invention. In particular, it is envisaged that the provision of an impedance based gas sensor in an integrated circuit may require sensor electrodes having some form of corrosion protection, regardless of the exact placement of those sensor electrodes. In some alternative configurations, the sensor electrodes may for instance be formed in a metallization stack beneath a passivation stack. An opening in the passivation layer can, in such examples, provide access for the sensor to receive the target gas.

Returning to FIG. 2, it can be seen that the gas sensor includes first and second sensor electrodes 10. The sensor electrodes are electrically conductive and can comprise a metal such as Al, Cu or W, or an alloy of Al and Cu. As noted above, these materials ease the manufacture of the integrated circuit because Al and Cu are commonly used in back end of line (BEOL) processing. Further examples of such electrically conductive materials include Ti, TiN, TiW, TiWN and SiCr.

The gas sensor also includes a gas sensitive material 12. The gas sensitive material 12 has an impedance that is sensitive to the presence of a target gas. By taking measurements of capacitance and resistance across the first and second capacitor electrodes 10, the gas sensor can determine the presence and concentration of the target gas.

First and second sensor electrodes 10 can be arranged on the substrate 2 having a configuration that optimises their surface area and spacing. For example, the first and second sensor electrodes 10 can be provided as a pair of sets of interdigitated fingers. Alternative configurations, such a simple pair of opposing plates, are also envisaged.

The first and second sensor electrodes 10 are enclosed in an electrically conductive corrosion protection material 14. The corrosion protection material acts to inhibit substances such as water and oxygen from reaching the material used to form the sensor electrodes 10. A typical thickness for the corrosion protection material can be 50-100 nm.

As can be seen from FIG. 2, each sensor electrode 10 is separately enclosed in its own portion of electrically conductive corrosion protection material. Accordingly, the corrosion protection material that encloses the first sensor electrode is not directly electrically connected to the protection material portion enclosing the second sensor electrode. Accordingly, the only electrical path between the first electrode and the second electrode passes through the gas sensitive material 12.

Figure 1:
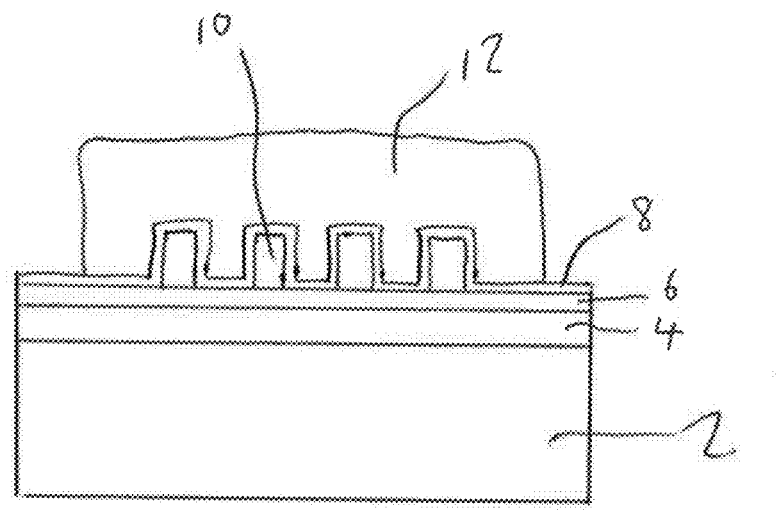
FIG. 1 shows an example of an integrated circuit including an environmental sensor.

The arrangement in FIG. 2 can be compared with, for example, the arrangement in FIG. 1. Were the corrosion protection material 14 in FIG. 2 to be provided as a single layer of the kind used for the protection layer 8 in FIG. 1, the electrical path from the first electrode to the second electrode through the gas sensitive material 12 would be short-circuited and current would flow only within the corrosion protection material 14. Correct operation of the sensor would therefore be prevented.

As noted above, suitable materials for the sensor electrodes 10 include metals such as Al, Cu and W. Suitable gas sensitive materials 12 can be selected in accordance with the target gas. Table 1 below indicates a range of target gases and the gas sensitive materials that can be used.

TABLE 1

Target Gases and Gas Sensitive Materials

| Target Gas | Gas Sensitive Material |
|---|---|
| Humidity | Metal oxides, PMMA, polysulfone, + conjugated polymers: doped polyaniline, Polyacetylene, PA, polypyrrole, Polythiophene, PTh Poly(3,4-ethylene-dioxythiophene), PEDOT Poly(phenyl vinlene), PPV |
| $CO_2$ | Metal oxides, emeraldine base polyaniline polymer, $In_2Te3$, polypyrrole polymer, Poly Ethylene Imine, N—N dimethylaminoethyl methacrylate and methyl methacrylate copolymer, . . . , other conjugated polymers |
| $O_2$ | Metal oxides, conjugated polymer such as polypyrrole, polyaniline, polythiophene and polyindole |
| Ethylene | Metal oxides |
| CO | Metal oxides, Polypyrrole based polymers, Polymer-Carbon Black Sensors, polyaniline semiconducting thin films, other conjugated polymers |
| $NH_3$ | Metal oxides, conjugated polymers such as Polyaniline |

With reference to Table 1, it is noted that in the case of "humidity", the target gas comprises a gas of individual water molecules. These molecules may, for example, be carried in air. These water molecules do not constitute water vapour as such, since they are not condensed into droplets of water.

Table 1 indicates the use of a range of metal oxides and conjugated polymers. For these materials, the selectivity for each target gas can be obtained by using dopants specific to the target gas, or combinations of polymers and/or metal oxides.

In the case of metal oxides, a paper by G. Eranna et al, entitled "Oxide materials for developments of integrated gas sensors—a comprehensive review", published in Critical review in solid state and material science, 29: 111-188, 2004, indicates a range of specific metal oxides that may be used, and the target gases to which they are applicable. In the case of conducting polymers, a paper by Hua Bai and Gaoquan Shi entitled "Gas Sensors Based on Conducting Polymers" published in Sensors 2007, 7, 267-307, includes (for example in table 3 thereof), a range of specific polymers that may be used, and the target gases to which they are applicable.

Suitable materials for the corrosion protection material 14 include, for example, TiN. Other examples for the corrosion protection material 14 include TaN, TiWN and also selectively deposited materials like e-less ternary materials such as CoWP, CoWB, NiMoP, NiMoB or multilayers of those ternary alloys.

It will be appreciated that a number of alternative ways can be used to enclose the sensor electrodes with the corrosion protection material. A number of alternative examples of such methods are described below in relation to FIGS. 3 to 9.

Figure 3:
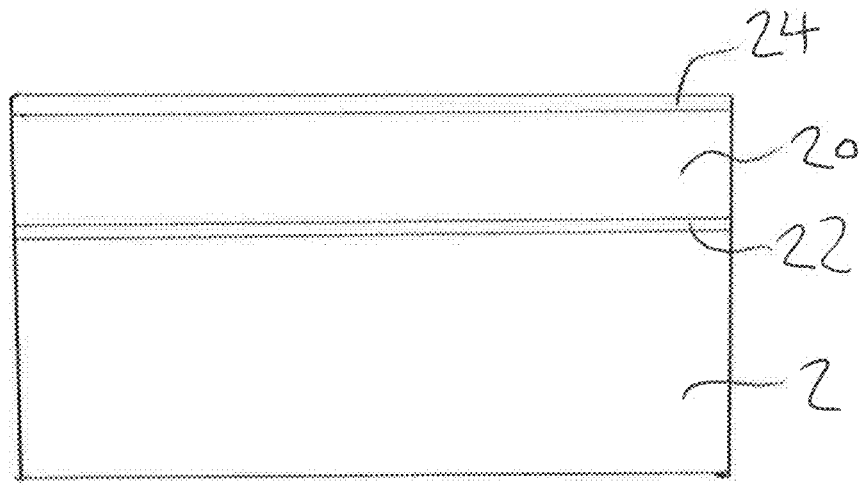
FIGS. 3 and 4 illustrate the steps in a process for forming part of the electrically conductive corrosion protection material enclosing each gas sensor electrode according to an embodiment of the invention.
Figure 4:
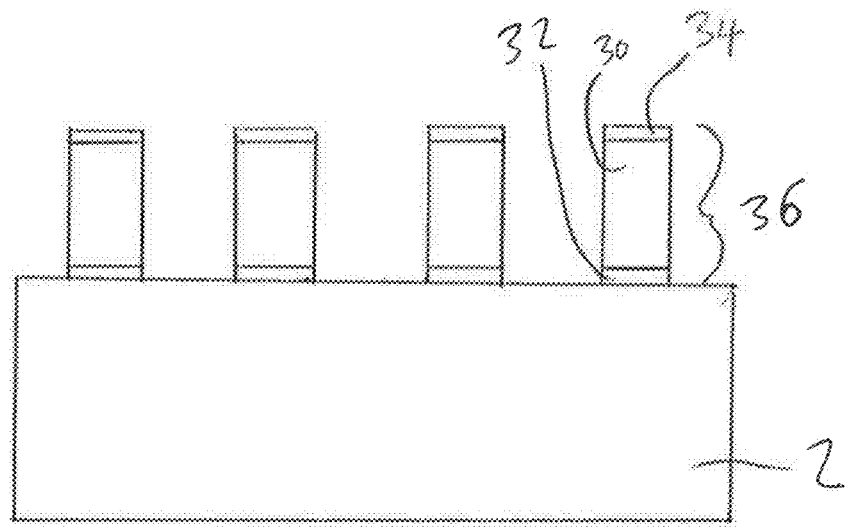

FIGS. 3 and 4 illustrate an example method that can be used to cover at least an underside of the sensor electrodes with the corrosion protection material. In the subsequent figures, the metallization stack and passivation stack shown in FIG. 2 are not illustrated. As noted above, these features are optional.

A first stage in a method for producing the sensor electrodes enclosed in a corrosion protection material is illustrated in FIG. 3. A semiconductor substrate 2 of the kind described above in relation to FIG. 2 is first provided. A stack of layers is then deposited on to the substrate 2. The stack of layers can include at least a first layer 22 of the electrically conductive corrosion protection material. Subsequently, an electrically conductive electrode layer 20 is deposited on to the first layer 22. In the present example, after the electrode layer 20 has been deposited, a second layer of the electrically conductive corrosion protective material is deposited onto the electrode layer 20. This second layer acts to enclose the top portion of the subsequently patterned electrodes. However, as described below, this second layer 24 is not essential in some embodiments.

After the layers 22, 20, 24 have been deposited, they can be patterned using standard lithographic techniques to form the sensor electrodes. As shown in FIG. 4, the sensor electrodes comprise a stack 36 of patterned layers including a first layer 32 of the electrically conductive corrosion protection material, an electrically conductive electrode layer 30 and, optionally, a second layer 34 of the electrically conductive corrosion protection material. In FIG. 4, the electrodes are arranged as interdigitated fingers, however the processing technique described here can also be used to provide electrodes having alternative arrangements.

The deposition and lithographic patterning steps described in relation to FIGS. 3 and 4 can provide corrosion protection for the underside and optionally the top side of the sensor electrodes. To provide corrosion protection for the sidewalls of the stacks 36, a number of alternative subsequent steps can be used. A first example is illustrated in FIGS. 5 and 6.

Figure 5:
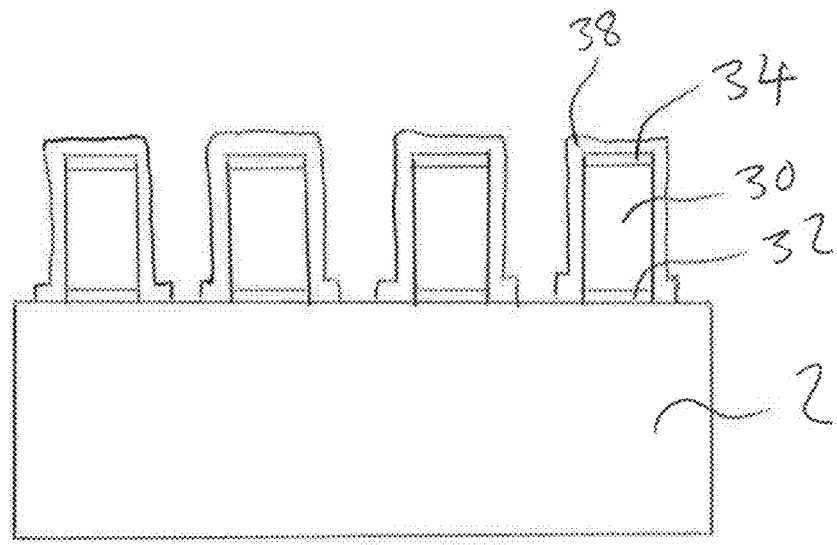
FIGS. 5 and 6 illustrate the steps in a process for forming the electrically conductive corrosion protection material on sidewalls of each gas sensor electrode according to an embodiment of the invention.
Figure 6:
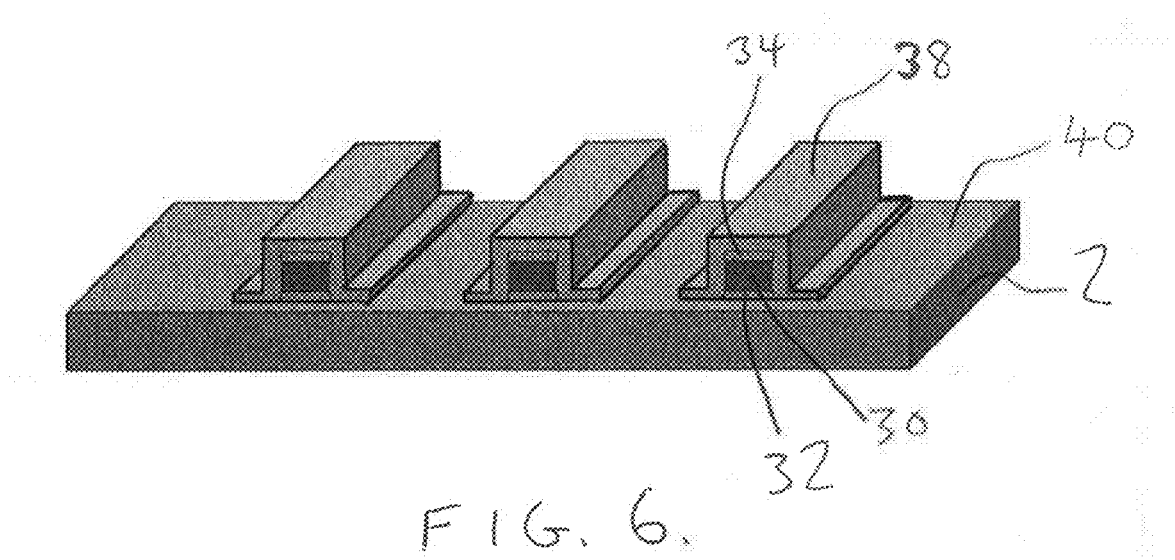

In FIG. 5, following the formation of the stacks 36 shown in FIG. 4, a further layer 38 of the electrically conductive corrosion protection material is deposited on to the substrate 2. This layer 38 substantially covers the major surface of the substrate including the stacks. At this stage, the layer 38 connects the adjacent stacks, whereby gas sensitive material provided in between the electrodes would be short-circuited. To avoid this problem, the portions of the layer 38 provided in the spaces between adjacent stacks can be removed by etching. A mask can be used to prevent etching of the gas sensitive material around the electrodes themselves. Following this etching step, a configuration of the kind illustrated in FIGS. 5 and 6 is reached. It can be seen from FIGS. 5 and 6 that when using the deposition of a layer 38 comprising the corrosion protection material that covers the stacks of the sensor electrodes and the substrate, it is not expressly required that the second optional layer of electrically conductive corrosion protection material 34 is provided.

Figure 7:
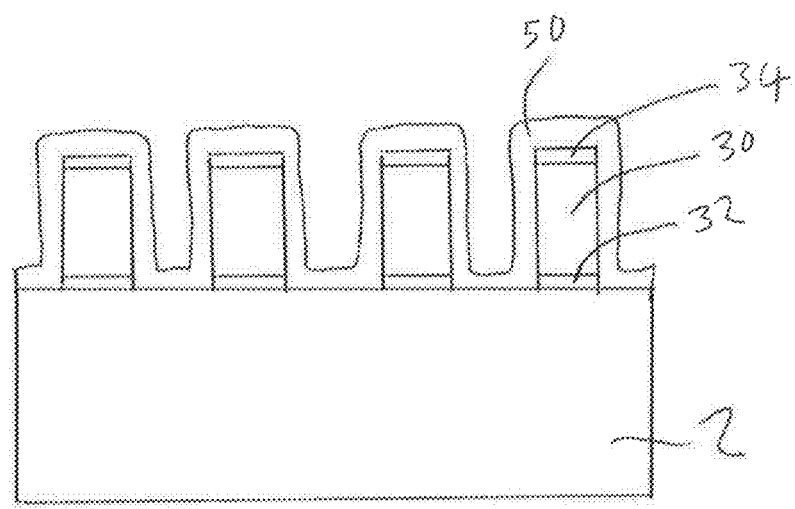
FIGS. 7 to 9 illustrate the steps in an alternative process for forming the electrically conductive corrosion protection material on sidewalls of each gas sensor electrode according to an embodiment of the invention.
Figure 8:
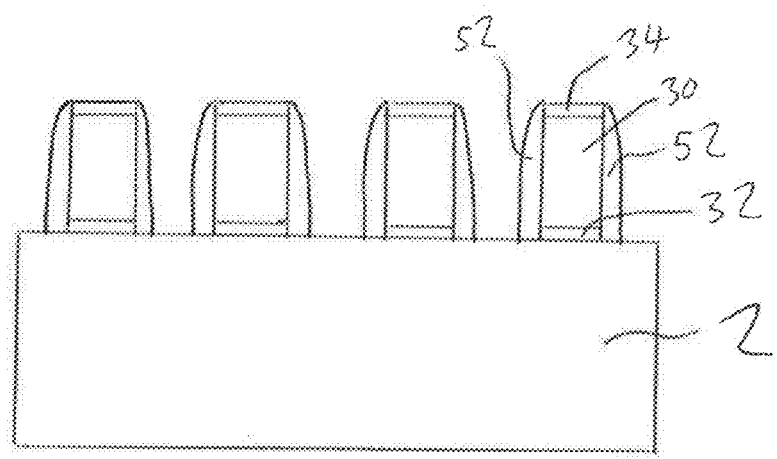
Figure 9:
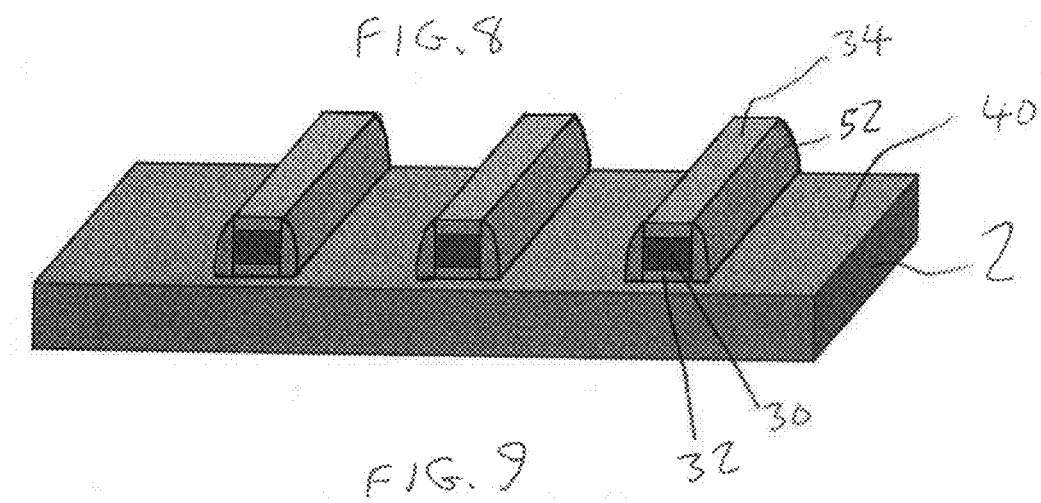

An alternative method for enclosing the sensor electrodes in the corrosion protection material is now described in relation to FIGS. 7 to 9.

In FIG. 7, following the above described steps for forming the arrangement of FIG. 4, the stacks 36 are covered with a layer 50 of the corrosion protection material.

This step can be viewed as analogous to the initial deposition step preceding FIG. 5. To remove the corrosion protection material from the areas between the various stacks on the substrate as shown in FIG. 5, it is necessary to use some form of mask to prevent etching of the material outside of the intervening portions on the substrate. The example illustrated in FIGS. 7 to 9 is simpler, in the sense that a mask of this kind is not required.

Following deposition of the corrosion protection material to reach the stage shown in FIG. 7, a directional etch is then used to remove the portions of the material that lie in intervening portions on the substrate. This etching step etches in a direction downwards towards the substrate 2, whereby material on top of the stacks and material in between the stacks tends to be etched away, while portions of the corrosion protection material on the side walls of the stacks are retained. The result of such etch is illustrated in FIGS. 8 and 9. This kind of etching sequence is analogous to that used to form spaces on the sides of gate stacks in CMOS transistors.

As illustrated in FIGS. 8 and 9, in the present example, since the directional etch removes material from the top of the stack, the second upper layer of corrosion protection material 34 provided in the steps described in relation to FIGS. 3 and 4, can ensure that at least some of the corrosion protection material remains at the top of the stack to ensure that the electrodes are enclosed.

The methodology shown in FIGS. 7 to 9 is therefore simpler than that described in relation to FIGS. 5 and 6, since fewer steps are required (e.g. no lithography is needed to remove parts of the corrosion protection material layer deposited over the stacks).

An integrated circuit of the kind described herein, can, for example, be incorporated into a radio frequency identification (RFID) tag. The sensor can be connected to circuitry of the RFID tag, including features such as an antenna to allow readout of sensing data collected by the sensor. Similarly, an integrated circuit of the kind described herein, may be incorporated into a mobile communications device such as a laptop, tablet or mobile telephone to allow the device to collect data relating to the presence of a target gas and use the data for various applications.

It is further envisaged that an integrated circuit of the kind described herein, could be incorporated into a heating, ventilation and air conditioning (HVAC) system. This would allow the HVAC system to collect information relating to the presence of one or more target gasses in the heating, ventilation or air conditioning of, for example, a building (for example a greenhouse or office building), or a vehicle such as an automobile or an aircraft.

Accordingly, there has been described an integrated circuit and a method of making the same. The integrated circuit includes a semiconductor substrate. The integrated circuit also includes an electrical impedance based gas sensor located on the substrate. The sensor includes first and second electrically conductive sensor electrodes. Each sensor electrode is enclosed in an electrically conductive corrosion protection material. The sensor also includes a gas sensitive material located between the sensor electrodes. The impedance of the gas sensitive material is sensitive to a gas to be sensed.

Although particular embodiments of the invention have been described, it will be appreciated that many modifications/additions and/or substitutions may be made within the scope of the claimed invention.

The invention claimed is:
1. An integrated circuit comprising:
a semiconductor substrate;
a metallization stack;
a passivation stack;

an electrical impedance based gas sensor located on top of the metallization and passivation stacks, the sensor comprising first and second electrically conductive sensor electrodes,
wherein the sensor electrodes are arranged on the substrate,
wherein each sensor electrode is enclosed in an electrically conductive corrosion protection material, and
wherein the electrically conductive corrosion protection material forms an enclosure of sidewalls and a top of the sensor electrodes; and
a gas sensitive material located between the sensor electrodes, wherein the impedance of the gas sensitive material is sensitive to a gas to be sensed,
wherein each sensor electrode enclosed in the electrically conductive corrosion protection material includes a stack comprising:
a first layer of the electrically conductive corrosion protection material;
an electrically conductive electrode layer on the first layer of the electrically conductive corrosion protection material; and
a second layer of the electrically conductive corrosion protection material on the electrically conductive electrode layer,
wherein the stack is coated with a further layer of the electrically conductive corrosion protection material.

2. The integrated circuit of claim 1, wherein sidewalls of the stack are covered by sidewall spacers of said electrically conductive corrosion protection material.

3. The integrated circuit of claim 1, wherein the sensor electrodes are arranged as a plurality of interdigitated fingers.

4. The integrated circuit of claim 1, wherein the sensor electrodes comprise Al.

5. The integrated circuit of claim 1, wherein the electrically conductive corrosion protection material comprises TiN.

6. A Radio Frequency Identification (RFID) tag comprising an integrated circuit according to claim 1.

7. A mobile communications device comprising an integrated circuit according to claim 1.

8. A heating, ventilation and air conditioning (HVAC) system comprising one or more integrated circuits according to claim 1.

9. The integrated circuit of claim 1, wherein the enclosure only protects the sidewalls and the top of the electrodes and does not completely encircle the electrodes.

10. A method of making an integrated circuit, the method comprising:
providing a semiconductor substrate, a metallization stack and a passivation stack;
forming an electrical impedance based gas sensor on top of the substrate metallization and passivation stacks, the sensor comprising first and second electrically conductive sensor electrodes,
wherein the sensor electrodes are arranged on the substrate,
wherein each sensor electrode is enclosed in an electrically conductive corrosion protection material, and
wherein the electrically conductive corrosion protection material forms an enclosure of sidewalls and a top of the sensor electrodes;
depositing a gas sensitive material located between the sensor electrodes, the gas sensitive material having an impedance that is sensitive to a gas to be sensed,
wherein forming the first and second electrically conductive sensor electrodes enclosed in the electrically conductive corrosion protection material comprises:
depositing a stack of layers comprising:
a first layer of the electrically conductive corrosion protection material;
an electrically conductive electrode layer on the first layer of the electrically conductive corrosion protection material; and
a second layer of the electrically conductive corrosion protection material on the electrically conductive electrode layer;
patterning the stack; and
coating the stack with a further layer of the electrically conductive corrosion protection material.

11. The method of claim 10, further comprising covering sidewalls of the stack with sidewall spacers of said electrically conductive corrosion protection material.

12. The method of claim 10, wherein the enclosure only protects the sidewalls and the top of the electrodes and does not completely encircle the electrodes.

13. An integrated circuit comprising:
a semiconductor substrate;
an electrical impedance based gas sensor located on a passivation layer on the substrate, the sensor comprising first and second electrically conductive sensor electrodes,
wherein the sensor electrodes are arranged on the substrate, and
wherein each sensor electrode is enclosed in an electrically conductive corrosion protection material, and
wherein the electrically conductive corrosion protection material forms an enclosure of sidewalls of the sensor electrodes and a top of the sensor electrodes; and
a gas sensitive material located between the sensor electrodes, wherein the impedance of the gas sensitive material is sensitive to a gas to be sensed,
wherein each sensor electrode enclosed in the electrically conductive corrosion protection material includes a stack comprising:
a first layer of the electrically conductive corrosion protection material;
an electrically conductive electrode layer on the first layer of the electrically conductive corrosion protection material; and
a second layer of the electrically conductive corrosion protection material on the electrically conductive electrode layer,
wherein the stack is coated with a further layer of the electrically conductive corrosion protection material, and
wherein sidewalls of the stack are covered by sidewall spacers of the electrically conductive corrosion protection material, the sidewall spacers being formed by covering the sidewalls of the stack with the electrically conductive corrosion protection material.

14. A method of making an integrated circuit, the method comprising:
providing a semiconductor substrate;
forming an electrical impedance based gas sensor on a passivation layer the substrate, the sensor comprising first and second electrically conductive sensor electrodes,
wherein the sensor electrodes are arranged on the substrate,
wherein each sensor electrode is enclosed in an electrically conductive corrosion protection material, and wherein the electrically conductive corrosion protection material forms an enclosure of sidewalls of the sensor electrodes and a top of the sensor electrodes; and depositing a gas sensitive material located between the sensor electrodes, the gas sensitive material having an impedance that is sensitive to a gas to be sensed, wherein forming the first and second electrically conductive sensor electrodes enclosed in the electrically conductive corrosion protection material comprises:

depositing a stack of layers comprising:
- a first layer of the electrically conductive corrosion protection material;
- an electrically conductive electrode layer on the first layer of the electrically conductive corrosion protection material; and
- a second layer of the electrically conductive corrosion protection material on the electrically conductive electrode layer;

patterning the stack;

coating the stack with a further layer of the electrically conductive corrosion protection material; and covering sidewalls of the stack with sidewall spacers of the electrically conductive corrosion protection material.

* * * * *